United States Patent
Bringley et al.

(10) Patent No.: US 7,306,777 B2
(45) Date of Patent: Dec. 11, 2007

(54) ANTIMICROBIAL COMPOSITION

(75) Inventors: Joseph F. Bringley, Rochester, NY (US); Yannick J. F. Lerat, Chalon-sur-Saone (FR); Nancy B. Liebert, Rochester, NY (US); Richard W. Wien, Pittsford, NY (US); David L. Patton, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 478 days.

(21) Appl. No.: 10/737,455

(22) Filed: Dec. 16, 2003

(65) Prior Publication Data
US 2005/0129766 A1 Jun. 16, 2005

(51) Int. Cl.
*C01B 25/45* (2006.01)

(52) U.S. Cl. ................ 423/306; 428/323

(58) Field of Classification Search ............ 424/70.11, 424/78.18, 604; 423/306
See application file for complete search history.

(56) References Cited

U.S. PATENT DOCUMENTS

| | | | | |
|---|---|---|---|---|
| 5,441,717 A | * | 8/1995 | Ohsumi et al. | 423/306 |
| 5,556,699 A | * | 9/1996 | Niira et al. | 428/323 |
| 6,225,394 B1 | * | 5/2001 | Lan et al. | 524/445 |
| 2003/0091767 A1 | | 5/2003 | Podhajny | |

FOREIGN PATENT DOCUMENTS

| | | |
|---|---|---|
| JP | 59-212405 | 12/1984 |
| JP | 04-006065 | 1/1992 |
| JP | 04-007335 | 1/1992 |
| JP | 04-089851 | 3/1992 |
| JP | 04-126529 | 4/1992 |
| JP | 04-126530 | 4/1992 |
| JP | 04007335 | * 10/1992 |
| JP | 06-079834 | 3/1994 |
| JP | 06-212003 | 8/1994 |
| JP | 06-263933 | 9/1994 |
| JP | 08-253637 | 10/1996 |
| JP | 10-034791 | 2/1998 |
| JP | 11-081159 | 3/1999 |
| JP | 2000-103014 | 4/2000 |
| WO | 9831731 | 7/1998 |
| WO | 2004063254 | 7/2004 |

OTHER PUBLICATIONS

U.S. Appl. No. 10/737,346 (entitled Antimicrobial Web for Application to a Surface, by Patton et al., filed Dec. 16, 2003.
U.S. Appl. No. 10/736,974 (entitled Antimicrobial Article With Diffusion Control Layer, by Bringley et al., filed Dec. 16, 2003.

* cited by examiner

*Primary Examiner*—Michael G. Hartley
*Assistant Examiner*—Jagadishwar Samala
(74) *Attorney, Agent, or Firm*—Andrew J. Anderson; Sarah Meeks-Roberts

(57) ABSTRACT

This invention relates to an antimicrobial composition comprising an antimicrobial compound and a polyethylene-polyvinylalcohol copolymer. It further relates to a medium having antimicrobial properties comprising a support and a layer comprising an antimicrobial composition comprising an antimicrobial compound and a polyethylene-polyvinylalcohol copolymer.

12 Claims, No Drawings

ANTIMICROBIAL COMPOSITION

FIELD OF THE INVENTION

The present invention relates to an antimicrobial composition having a controlled release of an antimicrobial compound; it further relates to a medium comprising said antimicrobial composition.

BACKGROUND OF THE INVENTION

In recent years people have become very concerned about exposure to the hazards of microbe contamination. For example, exposure to certain strains of *Eschericia coli* through the ingestion of undercooked beef can have fatal consequences. Exposure to *Salmonella enteritidis* through contact with unwashed poultry can cause severe nausea. Mold and yeast (*Candida albicans*) may cause skin infections. In some instances, biocontamination alters the taste of the food or drink or makes the food unappetizing. With the increased concern by consumers, manufacturers have started to produce products having antimicrobial properties. A wide variety of antimicrobial materials have been developed, which are able to slow or even stop microbial growth; such materials when applied to consumer items may decrease the risk of bacterial infection.

Noble metal ions such as silver and gold ions are known for their antimicrobial properties and have been used in medical care for many years to prevent and treat infection. In recent years, this technology has been applied to consumer products to prevent the transmission of infectious disease and to kill harmful bacteria such as *Staphylococcus aureus* and *Salmonella*. In common practice, noble metals, metal ions, metal salts, or compounds containing metal ions having antimicrobial properties may be applied to surfaces to impart an antimicrobial property to the surface. If, or when, the surface is inoculated with harmful microbes, the antimicrobial metal ions or metal complexes, if present in effective concentrations, will slow or even prevent altogether the growth of those microbes. Antimicrobial activity is not limited to noble metals but is also observed in organic materials such as triclosan, and some polymeric materials.

It is important that the antimicrobial active element, molecule, or compound be present on the surface of the article at a concentration sufficient to inhibit microbial growth. This concentration, for a particular antimicrobial agent and bacterium, is often referred to as the minimum inhibitory concentration (or MIC). It is also important that the antimicrobial agent be present on the surface of said article at a concentration significantly below that which may be harmful to the user of said article. This prevents harmful side effects of the article and decreases the risk to the user, while providing the benefit of reducing microbial contamination. More recently, metal ion exchange materials have been developed which are able to effect the so-called "controlled release" of an antimicrobial ion, by virtue of exchange of the antimicrobial ion with ions commonly present in biological environments. This approach is very general since innocuous ions such as sodium and potassium are present in virtually all biological environments. The approach has the advantage in that the antimicrobial ions are bound tightly by the ion exchange medium, but are released when exposed to conditions under which biological growth may occur.

U.S. patent application Ser. No. 0091767 A1 to Podhajny describes a method of applying an antimicrobial treatment to a packaging material, and to polymer dispersions containing antimicrobial zeolites. The zeolite containing dispersions may be formulated in water-based or solvent-based systems. Suitable polymers for practice of the invention listed are polyamides, acrylics, polyvinyl chloride, polymethyl methacrylates, polyurethane, ethyl cellulose, and nitro celluloses.

U.S. Pat. No. 5,556,699 to Niira et al describes transparent polymeric films containing antimicrobial zeolites which are ion exchanged with silver and other ions. The films are said to display antimicrobial properties. Polymeric materials suitable for the invention include ethylene ethyl acrylate (EEA), ethylene vinyl acetate (EVA), polyethylene, polyvinyl chlorides, polyvinyl fluoride resins, and others.

There is a problem in that the polymeric binder or polymeric medium may severely limit the release of the antimicrobial material. Therefore, the exchange of antimicrobial ions from the antimicrobial films may not be facile enough to achieve a concentration of antimicrobial metal ions sufficient to limit the growth rate of a particular microbe, or may not be above the minimum inhibitory concentration (MIC). Alternatively, there is a problem in that the rate of release of antimicrobial ions from antimicrobial films may be too facile, such that the antimicrobial film may quickly be depleted of antimicrobial active materials and become inert or non-functional. Depletion results from rapid diffusion of the active materials into the biological environment with which they are in contact. It is desirable that the rate of release of the antimicrobial ions or molecules be controlled such that the concentration of antimicrobials remains above the MIC. The concentration should remain there over the duration of use of the antimicrobial article. The desired rate of exchange of the antimicrobial may depend upon a number of factors including the identity of the antimicrobial metal ion, the specific microbe to be targeted, and the intended use and duration of use of the antimicrobial article.

PROBLEM TO BE SOLVED BY THE INVENTION

There remains a need to control the release of an antimicrobial active material from an article, such that a minimum inhibitory concentration of the antimicrobial metal may be achieved at the surfaces of the article for the duration of the use of said article, under the common operating environment of said article. There remains a further need to control the release of an antimicrobial active material from an article, such that the antimicrobially active material is not released too quickly, especially at levels significantly beyond the minimum inhibitory concentration, so that the activity of the article is long lasting, and further does not eliminate desirable microbial growth.

SUMMARY OF THE INVENTION

This invention provides an antimicrobial composition comprising an antimicrobial compound and a polyethylene-polyvinylalcohol copolymer. It further provides a medium comprising a support and a layer containing said composition.

This invention provides a useful antimicrobial composition suitable for many uses and particularly for the food industry. The polymer utilized in the composition is approved by the Food and Drug Administration (Sec 177.1360) for use with foodstuffs. The composition of the invention quickly provides a minimum inhibitory concentration of the antimicrobial metal at the surface of the medium containing said composition under the common operating environment of said medium. It provides this effect for a sustained period of time even at relatively low laydowns of silver ion.

DETAILED DESCRIPTION OF THE INVENTION

Articles having antimicrobial properties may be prepared by application of an antimicrobial compound (hereafter referred to as AMC) to the surface of the article, or by embedding an AMC within the article. In most instances, bacteria or microbes may reside only at the surface of an article, and thus the AMC is applied only to the surface. The AMC may be applied by many methods such as coating, spraying, casting, blowing, extruding, etc. Typically, the AMC is dissolved or dispersed in a vehicle (such as a solvent) and a binder (such as a polymer) which provides a means of adhering the AMC to the article surface. Alternatively, the AMC may be mixed or compounded directly within the polymer, and the mixture subsequently melted and extruded to form a film. The film may then be attached to an article by means such as gluing or lamination.

Upon use and exposure of an antimicrobial article to conditions under which microbial growth may occur, the AMC (or in the case of an antimicrobial metal ion exchange material, the antimicrobial metal ion) may then leach from the surface of the article to kill or inhibit the growth of microbes present thereon. In order for the article to have antimicrobial properties, the AMC must leach out at a rate fast enough to establish and maintain a minimum inhibitory concentration (MIC). Below the MIC, microbial growth may continue uninhibited. Likewise, it is important that the AMC not leach out so fast as to quickly deplete the article of AMC and thus limit the longevity of the effectiveness of the article. The rate at which the AMC may leach (or diffuse) is dependent upon its degree of solubilization in aqueous media (water). This is an essential point, since microbial growth requires high water activity commonly found in wet or humid environments. Because most antimicrobial materials are substantially soluble in water, the rate of diffusion of the AMC will be limited by the rate at which water can diffuse to the AMC and hence dissolve it. This is especially true for solid-phase AMC's, since diffusion may not occur until the AMC is dissolved or solubilized. If the AMC is embedded in a polymer which very quickly adsorbs water, the article may be quickly depleted of antimicrobial activity, since the AMC contained at its surface may quickly leach into the surrounding environment. Alternatively, if the AMC is embedded in a polymer which does not adsorb water, or only adsorbs water extremely slowly, then the AMC may diffuse very slowly or not at all, and a MIC may never be achieved in the surrounding environment. A measure of the permeability of various polymeric addenda to water is given by the permeability coefficient, P, which is given by $P$=(quantity of permeate)(film thickness)/[area×time× (pressure drop across the film)]

Permeability coefficients and diffusion data of water for various polymers are discussed by J. Comyn, in *Polymer Permeability*, Elsevier, New York, 1985 and in "Permeability and Other Film Properties of Plastics and Elastomers," Plastics Design Library, NY, 1995. The higher the permeability coefficient, the greater the water permeability of the polymeric media. The permeability coefficient of a particular polymer may vary depending upon the density, crystallinity, molecular weight, degree of cross-linking, and the presence of addenda such as coating-aids, plasticizers, etc.

The inventive composition comprises an antimicrobial compound and a polyethylene-polyvinylalcohol copolymer, wherein the antimicrobial compound is embedded in the copolymer. Either the compound itself or an antimicrobial moiety released from the antimicrobial compound is preferably aqueously soluble. The polyethylene-polyvinylalcohol copolymer is preferred because its water permeability is intermediate and thus it allows for facile diffusion of the AMC contained within, to the surface of an article. This allows for a MIC to be achieved at the surface without quickly depleting the article of all AMC. Thus, the antimicrobial properties of the article are long-lived. The polyethylene-polyvinylalcohol co-polymer may also serve as a binder to allow for adhesion of an AMC to a surface, article, or substrate. The fraction of polyvinyl alcohol in the copolymer should be from about 20% to 80%, and more preferably from about 45% to 75%. The copolymer may have a wide range of molecular weight, but it is preferred that the copolymer have an average molecular weight between 100,000 and 1,000,000. It is preferred that the water permeability coefficient of the polyethylene-polyvinylalcohol copolymer be from about 5000 to 15000 [(cm$^3$cm)/(cm$^2$sec/Pa)]×10$^{13}$.

To form the inventive composition, the antimicrobial compound should be uniformly and homogeneously mixed within the polyethylene-polyvinylalcohol copolymer. Mixing may be accomplished by a number of methods. For example, the copolymer and the AMC may be dispersed in a suitable solvent and then coated or dried to form a solid mixture. Typically, the solvent will be a alcohol/water mixture. The process may include the addition of surfactants, peptizers, dispersion aids, etc. to facilitate the mixing. Alternatively the mixture may be formed by directly compounding the polymer and AMC at the melting temperature of the polymer as is done by screw compounding.

The antimicrobial active compound of the antimicrobial composition may be selected from a wide range of known antibiotics and antimicrobials. Suitable materials are discussed in "Active Packaging of Food Applications" A. L. Brody, E. R. Strupinsky, and L. R. Kline, Technomic Publishing Company, Inc. Pennsylvania (2001). Examples of antimicrobial agents suitable for practice of the invention include benzoic acid, sorbic acid, nisin, thymol, allicin, peroxides, imazalil, triclosan, benomyl, antimicrobial metal-ion exchange material, metal colloids, metal salts, anhydrides, and organic quaternary ammonium salts.

In a preferred embodiment, the antimicrobial compound is selected from metal ion-exchange materials which have been exchanged or loaded with antimicrobial ions. Metal ion-exchange materials suitable for practice of the invention are selected from zirconium phosphates, metal hydrogen phosphates, sodium zirconium hydrogen phosphates, zeolites, clays such as montmorillonite, ion-exchange resins and polymers, porous alumino-silicates, layered ion-exchange materials, and magnesium silicates. Preferred metal ion exchange materials are zirconium phosphate, metal hydrogen phosphate, sodium zirconium hydrogen phosphate, or zeolite. Preferred antimicrobial ions are silver, copper, nickel, zinc, tin, and gold. In a particularly preferred embodiment the antimicrobial ions are selected from silver and zinc. The antimicrobial ion is the antimicrobial moiety of the antimicrobial compound. In yet another preferred embodiment the antimicrobially active compound is represented by the general formula:

$M(H_{1-x-y}Na_xAg_yPO_4)_2.H_2O;$ wherein M=Ti and Zr and x and y are greater than zero and less than one. An example preparation of this material is given in the example section, and the preparation of these material are discussed at length in U.S. application Ser. No. 10/324,234 85124 filed Dec. 19, 2002.

The antimicrobial compound, particularly an antimicrobial metal ion exchange material, is preferably 0.1 to 5.0% by weight of the composition. It is preferred, when the antimicrobial ion is silver, that the silver ion comprises 0.01 to 1.0% by weight of the composition.

The inventive composition may be applied to the surfaces of walls, countertops, floors, furniture, consumer items, packaging, medical products such as bandages, garments, prosthetics, etc. to prevent the growth of microbes such as bacteria, mold, and yeast and to reduce the risk of the transmission of infectious disease. The inventive composition may be applied by many methods such as painting, spraying, casting, molding, blowing, coating, extruding, etc. Alternatively, the inventive coating may be applied to a substrate such as a plastic film and the film fastened to an article by means of lamination or gluing.

This invention further relates to an antimicrobial medium, preferably a film, comprising a support and an antimicrobial layer comprising the above-described antimicrobial composition. Examples of supports useful for practice of the invention are resin-coated paper, paper, polyesters, or microporous materials such as polyethylene polymer-containing material sold by PPG Industries, Inc., Pittsburgh, Pa. under the trade name of Teslin®, Tyvek® synthetic paper (DuPont Corp.), and OPPalyte® films (Mobil Chemical Co.) and other composite films listed in U.S. Pat. No. 5,244,861. Opaque supports include plain paper, coated paper, synthetic paper, photographic paper support, melt-extrusion-coated paper, and laminated paper, such as biaxially oriented support laminates. Biaxially oriented support laminates are described in U.S. Pat. Nos. 5,853,965; 5,866,282; 5,874,205; 5,888,643; 5,888,681; 5,888,683; and 5,888,714, the disclosures of which are hereby incorporated by reference. These biaxially oriented supports include a paper base and a biaxially oriented polyolefin sheet, typically polypropylene, laminated to one or both sides of the paper base.

Transparent supports include glass, cellulose derivatives, e.g., a cellulose ester, cellulose triacetate, cellulose diacetate, cellulose acetate propionate, cellulose acetate butyrate; polyesters, such as poly(ethylene terephthalate), poly(ethylene naphthalate), poly(1,4-cyclohexanedimethylene terephthalate), poly(butylene terephthalate), and copolymers thereof; polyimides; polyamides; polycarbonates; polystyrene; polyolefins, such as polyethylene or polypropylene; polysulfones; polyacrylates; polyether imides; and mixtures thereof. The papers listed above include a broad range of papers, from high end papers, such as photographic paper to low end papers, such as newsprint. Another example of supports useful for practice of the invention is fabrics such as wools, cotton, polyesters, etc.

In a suitable embodiment the antimicrobial layer has a thickness in the range of 0.1 μm to 100 μm, and more preferably the thickness of said antimicrobial layer is about 1 μm to 10 μm. Generally the support has a thickness in the range of 0.025 mm to 5 mm. In a preferred embodiment utilizing an antimicrobial ion exchange material, wherein silver is the antimicrobial ion, the silver laydown is preferably from 1 mg/m² to 1000 mg/m². The medium may then be attached to the surface of an article to impart antimicrobial activity to that item. The antimicrobial layer should be placed such that it is the outermost surface of the article to maximize its antimicrobial activity. The medium may be attached by any means such as lamination, gluing, wrapping, etc.

In the practice of the invention, a vehicle may be used to facilitate adhesion or application of the inventive composition or inventive medium to a surface, a fabric, or article to impart antimicrobial activity to that item. The vehicle serves multiple purposes including aiding the application of the antimicrobial composition via painting, spraying, coating, etc, binding the antimicrobial to that surface, and preventing the loss of antimicrobial activity due to normal wear or use. The vehicle used may be a polymer, a polymeric latex, a polymeric resin, an adhesive, or a glass or ceramic vehicle; i.e., the vehicle should comprise no more than 40% of the vehicle/antimicrobial composition mixture.

The following examples are intended to illustrate, but not to limit the invention:

EXAMPLES

Preparation of Silver ion Sequester/Release dispersion: Into a 1.0 L container was placed 100.00 g of amorphous $Zr(HPO_4)_2 \cdot H_2O$ (from MEI corporation) in 200.0 g of distilled water. To this suspension was added slowly, (over 5'): 133 ml (146.3 g) of 2.5 M NaOH. The pH was 7.7 @ 34° C. Then, with stirring, were simultaneously added: 166 ml (208.3 g) of 1.5 M AgNO3 at 8.3 ml/min for 20 minutes and 330.0 ml (336.3 g) 0.25 M NaOH at 16.5 ml/min for 20 minutes. The pH was maintained at about 5.0 throughout the addition. The contents were then allowed to stir overnight @ 40° C. The final pH was 5.20. Silver analysis indicated the final dispersion to be 2.71 weight % Ag. The final silver ion sequester and release agent material composition was calculated to be $Zr(H_{0.41}Ag_{0.37}Na_{0.22}PO_4)_2 \cdot H_2O$.

Example 1

Samples and Comparison Samples (C1-C5, E1 and E2)

The experiments were performed by forming a coating solution of $Zr(Ag_{0.37}, Na_{0.22}, H_{0.41}PO_4)_2 \cdot H_2O$ and the indicated polymer (Table 1) in an appropriate solvent. For PVA, water was used; for EVOH, a 50:50 mixture of water and isopropanol was used; and for all others acetone was used as the solvent. The coating solution was then applied onto a clean plastic support using a doctor blade having a 125 micron gap, and dried to form a film. In each case, the thickness of the film was between 5 and 6 microns. A 5 cm×5 cm piece of this film was then immersed in 25.0 ml of aqueous 0.1 M $NaNO_3$, allowed to remain suspended there for the indicated time (Table 1), and the silver concentration in the aqueous medium was then determined by atomic emission spectroscopy.

TABLE 1

Percentage of antimicrobial silver ion released over time for Samples (E1-E2) and comparison Samples (C1-C5).

| Sample or Comparison | Polymer or Resin | Permeability Coefficient, $P \times 10^{13}$ | Silver Laydown, (μg/cm²) | % Ag Release in time 1 h | 1 d | 4 d |
|---|---|---|---|---|---|---|
| C1 | PVA | 42,000 | 1.4 | 90 | 100 | — |
| C2 | PVA | 42,000 | 6.9 | 32 | 36 | 70 |
| E1 | EVOH | 10,000 | 1.2 | 40 | 65 | 100 |
| E2 | EVOH | 10,000 | 11.6 | 14 | 38 | 43 |
| C3 | CA | 5,500 | 12.0 | 2 | 15 | 21 |

TABLE 1-continued

Percentage of antimicrobial silver ion released over time for Samples (E1-E2) and comparison Samples (C1-C5).

| Sample or Comparison Sample | Polymer or Resin | Permeability Coefficient, $P \times 10^{13}$ | Silver Laydown, ($\mu g/cm^2$) | % Ag Release in time | | |
|---|---|---|---|---|---|---|
| | | | | 1 h | 1 d | 4 d |
| C4 | PMM | 480 | 28.7 | 2 | 7 | 7 |
| C5 | KYNAR | <5 | 27.4 | 0 | 1 | 6 |

The permeability coefficient is taken from S. Pauly in "Permeability and Diffusion Data", PVA is polyvinylalcohol, EVOH is polyethylene polyvinylalcohol copolymer, CA is cellulose acetate, PMM is polymethylmethacrylate, KYNAR is poly(vinylidenefluoride-co-tetrafluoroethylene).

The results of Table 1 indicate that the exchange rate of antimicrobial silver to the surrounding medium is strongly dependent upon the water permeability of the polymer. The results show that coatings of antimicrobial materials in polymers having a high permeability of water may quickly reach the minimum inhibitory concentration of antimicrobial. However, the activity of such coatings will be short lived due to depletion of silver ion, and consumption of the silver ion by bacteria and other microbes. The results further show that coatings of antimicrobials in polymers having low permeability to water have a much slower rate of exchange of the antimicrobial to the surrounding medium. For these coatings, a MIC may never be achieved, even when the silver concentration (or laydown in Table 1) is very high. The coatings of the inventive examples show a consistent, sustained release of the antimicrobial silver ion and, therefore, are most suitable as antimicrobial surfaces. The utility of the invention becomes yet more apparent in the following examples.

Example 2

Samples and Comparison Samples (E3-E4, C6-C9)

The antimicrobial activity of the coatings, (E3-E4, C6-C9), prepared as described above and as indicated in Table 2, were tested according to AATCC 147 and ASTM E2149-01 normalized methods adapted to coated antimicrobials. The principle of the test is to measure the activity of a leaching antimicrobial by the presence of a zone of inhibition at the surface of a Petri Dish inoculated with an appropriate micro-organism. Trypcase Soy Agar (TSA) solid growth medium was used. It was inoculated by a registered strain of Pseudomonas aeruginosa (ATCC 27853) from U.S. cultures. This bacteria type is a good representative of Gram negative bacteria, which is commonly used in antimicrobial testing. When the Petri dish was inoculated, a 2.5 cm disk of antimicrobial coating was set at its surface, with the active antimicrobial layer facing the growth medium surface. Then the plate was incubated at 30° C. for several days. After the period indicated in Table 2, the culture was examined for a zone of inhibition around the disk. A zone of inhibition is an area around the disk in which bacteria do not grow due to the antimicrobial activity of the coating. The larger the zone of inhibition, the greater the antimicrobial property of the coating.

TABLE 2

Zone of inhibition size (in cm) for coatings at various times.

| Sample or Comparison Sample | Polymer and Silver Laydown ($\mu g/cm^2$) | ZI (cm) after 1 day | ZI (cm) after 2 days | ZI (cm) after 3 days | ZI (cm) after 4 days |
|---|---|---|---|---|---|
| E3 | EVOH | 5.8 | 0.6 | 0.5 | 0.4 | 0.3 |
| E4 | EVOH | 11.6 | 0.9 | 0.9 | 0.7 | 0.6 |
| C6 | KYNAR | 1.4 | 0 | 0 | 0 | 0 |
| C7 | KYNAR | 16.1 | 0 | 0 | 0 | 0 |
| C8 | PMM | 11.8 | 0.4 | 0.3 | 0.1 | 0.1 |
| C9 | CA | 19.4 | 0 | 0 | 0 | 0 |

The permeability coefficient is taken from S. Pauly in "Permeability and Diffusion Data", PVA is polyvinylalcohol, EVOH is polyethylene polyvinylalcohol copolymer, CA is cellulose acetate, PMM is polymethylmethacrylate, KYNAR is poly(vinylidenefluoride-co-tetrafluoroethylene).

The data of Table 2 show that the inventive samples have very large and sustained zones of inhibition when the silver laydown is above about 5 $\mu g/cm^2$. In contrast, the comparative samples show no or very little zone of inhibition even when the silver concentration is very high.

The invention has been described in detail with particular reference to certain preferred embodiments thereof, but it will be understood that variations and modifications can be effected within the spirit and scope of the invention.

What is claimed is:

1. An antimicrobial composition comprising an antimicrobial compound and a polyethylene-polyvinylalcohol copolymer; wherein the antimicrobial compound is represented by the general formula:

$$M(H_{1-x-y}Na_xAg_yPO_4)_2 \cdot H_2O$$

wherein M is selected from Ti and Zr, and x and y are greater than zero and less than one; wherein the polyvinylalcohol content is from 20 to 80% by weight of the polyethylene-polyvinylalcohol copolymer; wherein the average molecular weight of the polyethylene-polyvinylalcohol copolymer is 100,000 to 1,000,000; and wherein the water permeability coefficient of the copolymer is from 5000 to 15000 $[(cm^3 cm)/(cm^2 sec/Pa)] \times 10^{13}$.

2. The composition of claim 1 wherein the antimicrobial compound is 0.1 to 5.0% by weight of the composition.

3. The composition of claim 1 wherein the silver ion of the antimicrobial compound comprises 0.01 to 1.0% by weight of the composition.

4. The composition of claim 1 wherein the polyvinylalcohol content is from about 45 to 75% by weight of the polyethylene-polyvinylalcohol copolymer.

5. A medium having antimicrobial properties comprising a support and a layer comprising an antimicrobial composition comprising an antimicrobial compound and a polyethylene-polyvinylalcohol copolymer; wherein the antimicrobial compound is represented by the general formula:

$$M(H_{1-x-y}Na_xAg_yPO_4)_2 \cdot H_2O$$

wherein M is selected from Ti and Zr, and x and y are greater than zero and less than one; wherein the polyvinylalcohol content is from 20 to 80% by weight of the polyethylene-polyvinylalcohol copolymer; wherein the average molecular weight of the polyethylene-polyvinylalcohol copolymer is 100,000 to 1,000,000; and wherein the water permeability coefficient of the copolymer is from 5000 to 15000 $[(cm^3 cm)/(cm^2 sec/Pa)] \times 10^{13}$.

6. The medium of claim 5 wherein the support layer is made from one or more of the following:

resin-coated paper,
paper, polyesters,
microporous materials,
polyethylene,
plain paper,
coated paper,
synthetic paper,
photographic paper support,
melt-extrusion-coated paper,
laminated paper,
biaxially oriented polyolefin,
polypropylene,
glass,
cellulose derivatives, or
polyesters.

7. The medium of claim 5 wherein the antimicrobial layer has a thickness in the range of 0.1 μm to 100 μm.

8. The medium of claim 5 where the thickness of said antimicrobial layer is about 1 μm to 10 μm.

9. The medium of claim 5 wherein the support layer has a thickness in the range of 0.025 mm to 5 mm.

10. The medium of claim 5 wherein the antimicrobial compound is 0.1 to 5.0% by weight of the antimicrobial composition.

11. The medium of claim 5 wherein the antimicrobial compound provides a silver laydown from 1 $mg/m^2$ to 1000 $mg/m^2$.

12. The medium of claim 5 wherein the polyvinylalcohol content is from about 45 to 75% by weight of the polyethylene-polyvinylalcohol copolymer.

* * * * *